United States Patent [19]

Katsumata et al.

[11] Patent Number: 5,078,149
[45] Date of Patent: Jan. 7, 1992

[54] ULTRASONIC COUPLER AND METHOD FOR PRODUCTION THEREOF

[75] Inventors: Hiroshi Katsumata; Hiroyuki Yagami; Tadashi Fujii; Toru Kawashima, all of Ashigarakami, Japan

[73] Assignee: Terumo Kabushiki Kaisha, Tokyo, Japan

[21] Appl. No.: 589,525

[22] Filed: Sep. 28, 1990

[30] Foreign Application Priority Data

Sep. 29, 1989 [JP] Japan .................. 1-254034
Sep. 29, 1989 [JP] Japan .................. 1-254035
Sep. 29, 1989 [JP] Japan .................. 1-254036

[51] Int. Cl.⁵ .................................. A61B 8/00
[52] U.S. Cl. .................. 128/662.03; 128/663.01; 73/644
[58] Field of Search ........... 128/662.03, 662.02, 128/662.06, 663.01; 73/644, 605

[56] References Cited

U.S. PATENT DOCUMENTS

| 3,394,586 | 7/1968 | Cross | 73/644 |
| 4,579,123 | 4/1986 | Chen et al. | 128/662.03 |
| 4,603,701 | 8/1986 | Chen | 128/662.03 |
| 4,796,632 | 1/1989 | Boyd et al. | 128/662.03 |
| 4,867,169 | 9/1989 | Machida et al. | 128/662.03 |

Primary Examiner—Francis Jaworski
Assistant Examiner—George Manuel
Attorney, Agent, or Firm—Burns, Doane, Swecker & Mathis

[57] ABSTRACT

An ultrasonic coupler provided with an ultrasonic wave propagating member formed of a water-containing polymeric gel and a holder for accommodating said propagating member and fixing it to a probe, which ultrasonic coupler is intended to be interposed between a subject under test and an ultrasonic probe for transmitting and receiving an ultrasonic wave to and from the subject under test and characterized by the fact that said ultrasonic wave propagating member is a water-containing polymeric gel produced by integrally cross-linking an aqueous solution of a water-soluble polymeric compound with said holder inside said holder.

13 Claims, 5 Drawing Sheets

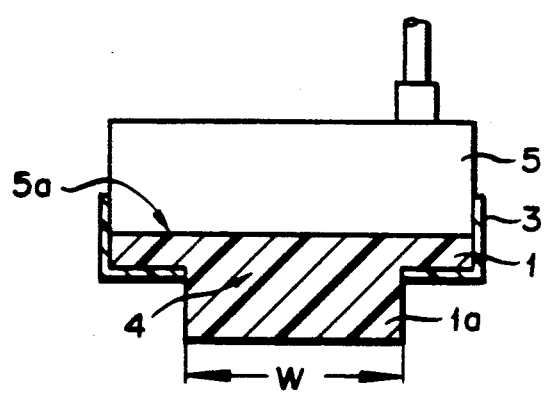
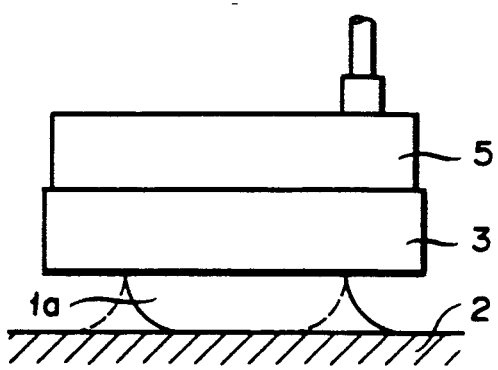
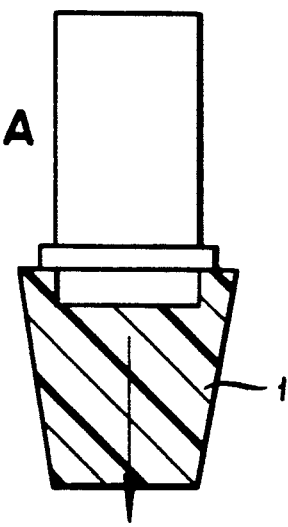
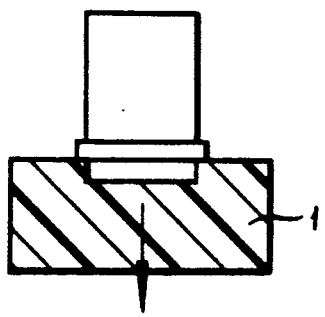
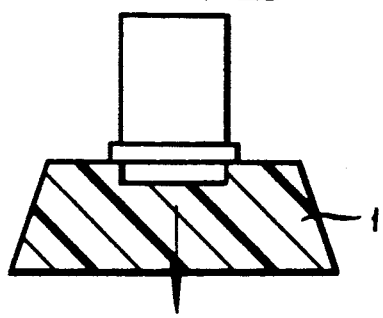

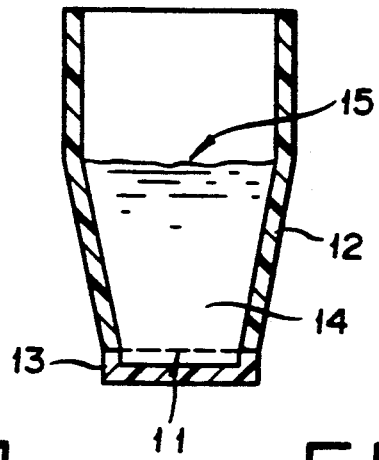
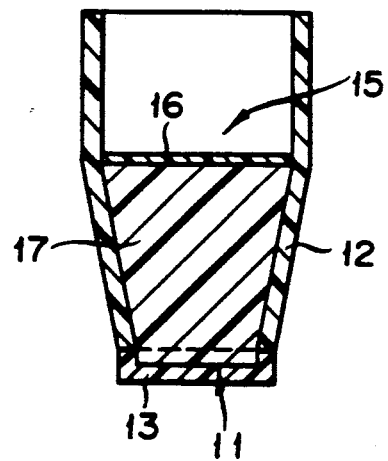
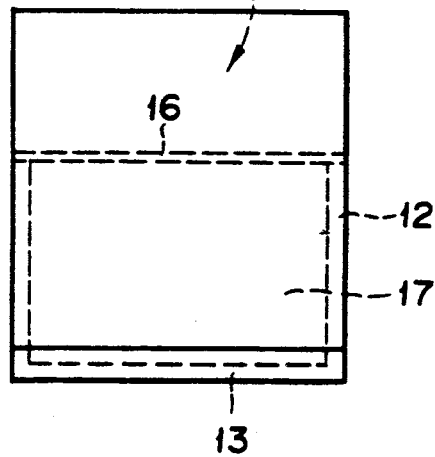
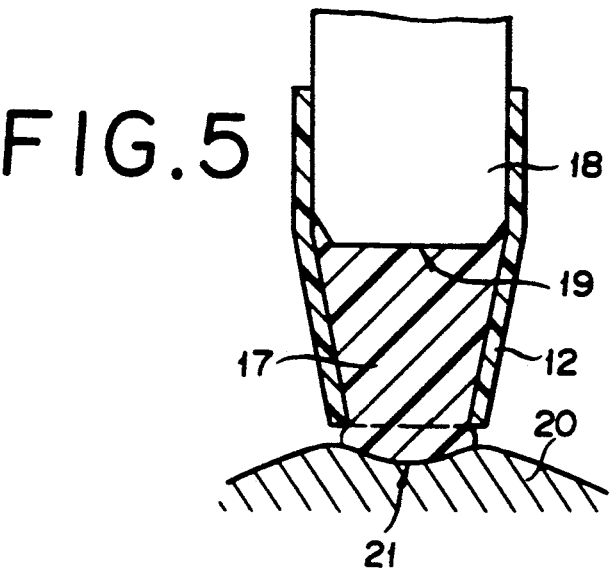

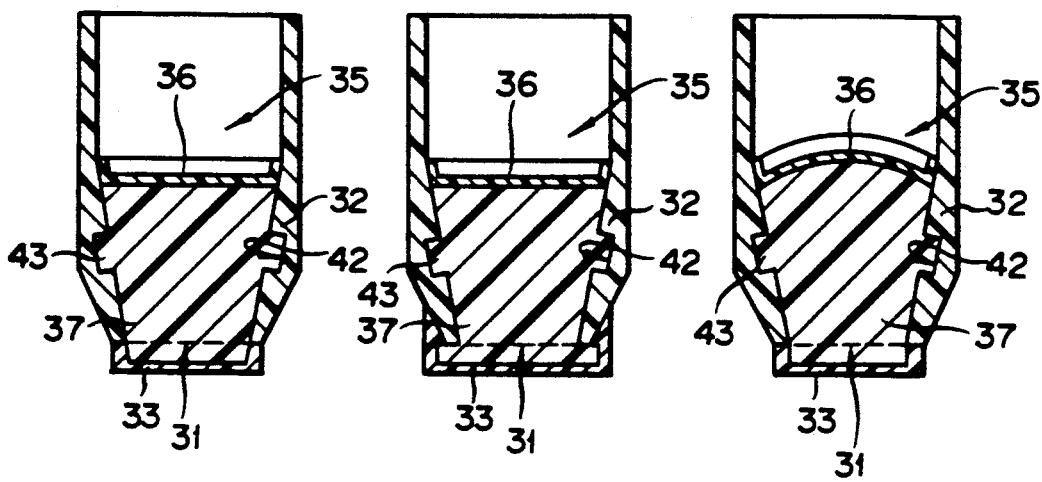
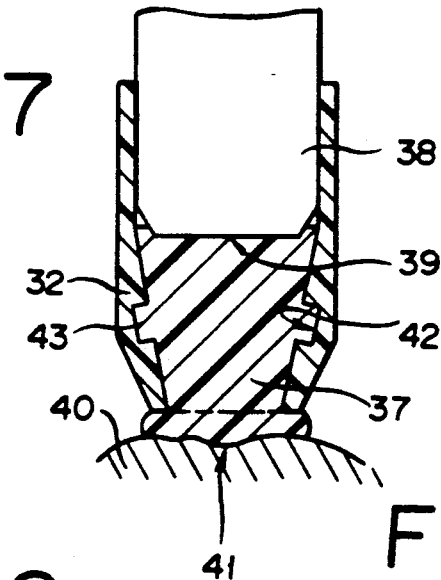
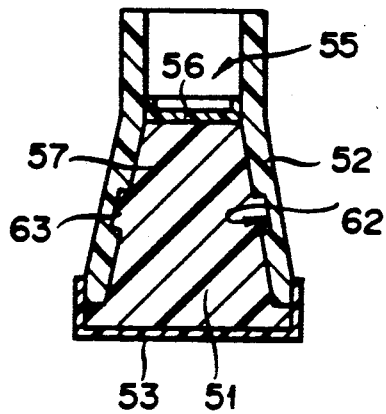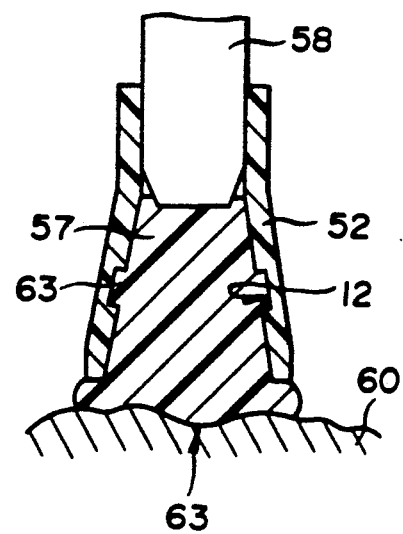

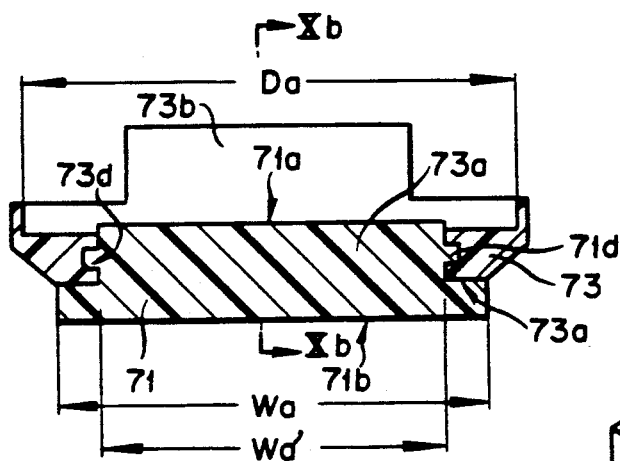
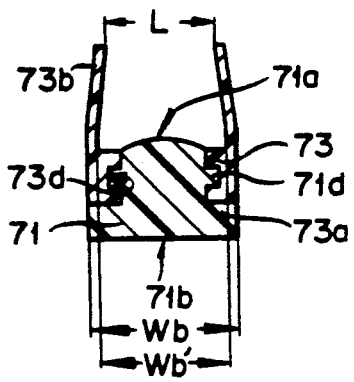
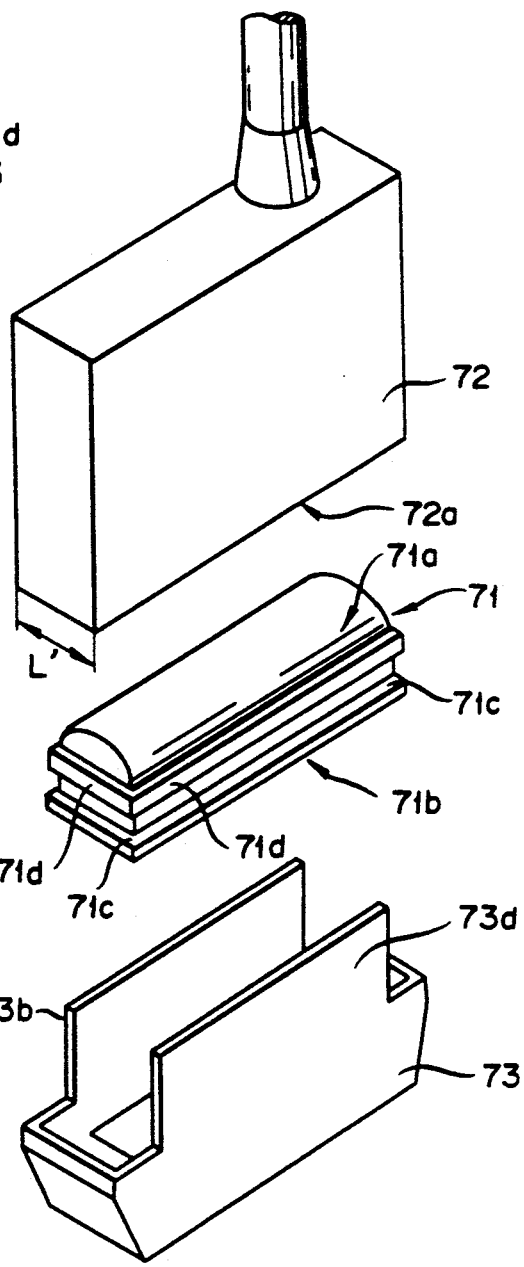

ULTRASONIC COUPLER AND METHOD FOR PRODUCTION THEREOF

BACKGROUND OF THE INVENTION

1. Field of the Invention

This invention relates to an ultrasonic coupler and a method for the production thereof More particularly, it relates to an ultrasonic coupler to be interposed between an ultrasonic probe used in the field of bioinstrumentation utilizing an ultrasonic wave and the surface of contact of a probe with an analyte under test and to a method for the production thereof.

2. Description of the Prior Art

The ultrasonic diagnostic apparatus, owing to the simplicity of handling and the obviation of the necessity for penetrating a patient's body, has found utility in numerous fields of diagnosis represented by those directed to the abdominal organs such as the heart and the liver.

In the case of a patient of cardiac disorder, to ensure precise performance of cardiotomy, the location and shape of a lesin, the relation of the lesion to normal parts adjoining it, and so on are preferable to be diagnozed in detail in advance of the operation. Particularly in the case of a neonate suffering from a serious cardiac disorder, this detailed diagnosis constitutes an important matter deciding between success and failure of the outcome of the surgical operation. The accurate preoperative diagnosis realized by the use of the ultrasonic diagnostic apparatus has been contributing conspicuously to improving the results of such surgical operations in recent years. By the preoperative sonic examination performed with a probe applied to the walls of the chest covering the heart but avoiding the lungs and the osseous tissues, no sufficient information can be obtained about cardiac diseases and lesions. As a way of making an ultrasonic diagnosis in detail beyond the limits of the sonic examination, the ultrasonic examination to be performed during the course of a cardiotomy may be conceived. When the ultrasonic examination is performed after a mediad incision of the sternum by directly applying a probe externally on the pericardium, the heart, or the blood vessel prior to the incision thereof affords the surgeon a detailed surgically useful diagnosis concerning the pertinent internal cavity. Further, the diagnosis enables the surgeon, in the course of operation, to confirm whether or not the surgical treatment initiated in consequence of the ultrasonic examination is adequate. This fact is important for preventing repetition of surgical operations and conducting postoperative management of the operated organ.

In the ultrasonic diagnosis, a cross-sectional image of a living body is obtained by a process which comprises projecting an ultrasonic pulse toward the interior of the body from the surface of the body or the surface of a relevant organ and receiving a reflected wave to be produced by the difference between acoustic impedances proper to varying tissues within the living body. For the purpose of obtaining an exact cross-sectional image, therefore, it is necessary that the ultrasonic probe should be applied to the surface of a body or the surface of a relevant organ tightly enough to preclude intervention of an air layer which exhibits a high reflectance to the ultrasonic wave.

When the probe is applied directly to the surface of a body as described above, however, the blood vessels and other tissues near the body surface are reproduced in the image in a shape deformed by pressure. When the ultrasonic examination is carried out by directly applying the probe to the heart or the wall of a blood vessel, the image is liable to register signs of arrhythmia and lowered blood pressure because the heart and the blood vessel are producing ununiform motions with an accompaniment of heartbeats and further because the probe exerts pressure on the surface of contact. It is, therefore, difficult to ensure safe use of the probe of the conventional type provided with a contact surface incapable of deformation by keeping this probe incessantly in tight contact with the surface of the heart or some other similar pulsating organ. In the existing true state of affairs, the usefulness of the real-time ultrasonic cross-section examination method to be performed during the course of a surgical operation is not manifested fully satisfactorily.

This situation is in need of a proper contact medium to be used between the probe and the surface of the body or the surface of a relevant organ, namely an ultrasonic coupler which possesses suppleness enough to follow the motion of the surface of the heat, for example, while remaining in tight contact therewith and excels in ultrasonic properties.

In the conventional ultrasonic coupler of this kind, a projected part 1a of the portion of an elastic acoustic medium 1 which is destined to contact a subject 2 under test is projected from an opening 4 on the subject side of an immobilizing member 3 in the same width as the width W of the opening, namely in the identical area with the area of the opening as illustrated in FIG. 1A and FIG. 1B (JP-A-61-288,840(1986)). The surface of the elastic acoustic medium 1 which contacts an ultrasonic wave-receiving surface 5a of an ultrasonic probe 5 has a flat shape. Further, no unified method has been established as to attaching means and positioning means employed for the attachment of an ultrasonic coupler to the ultrasonic probe 5. No unified method has yet been established as to means for stowing the elastic medium 1 in the immobilizing member 3.

With respect to the shape of the ultrasonic coupler, an ultrasonic coupler so shaped that the cross section of the elastic acoustic medium 1 taken perpendicularly to the direction of ultrasonic scanning decreases in width in the direction of transmission of ultrasonic wave as illustrated in FIG. 2A, FIG. 2B and FIG. 2C (JP-A-63-36,173(1988)) and an ultrasonic coupler so shaped that the cross section of the elastic acoustic medium 1 taken parallelly to the direction of ultrasonic scanning and also to the direction of ultrasonic wave transmission has a rectangular shape or has a width increasing in the direction of the ultrasonic wave transmission (JP-A-63-117,7345(1988)). The conventional ultrasonic couplers of this kind invariably have an elastic acoustic medium 1 projected toward the subject side from the immobilizing member.

Where the elastic acoustic medium projects from the subject side opening of the immobilizing member in the same width as the width of the opening as found in the conventional ultrasonic couplers, however, a movement of the ultrasonic coupler on the subject 2 results in impairment of a produced image because the elastic acoustic medium 1 is inevitably flexed and the desired transmission and reception of an ultrasonic wave is consequently obstructed as illustrated in FIG. 1B. Otherwise, the flexure of the elastic acoustic medium 1 poses a problem that the elastic acoustic medium eventually sustains breakage. Further, since the surface of the elastic acoustic medium 1 destined to contact the surface of the ultrasonic probe 5 for transmitting and receiving an ultrasonic wave is flat, bubbles (air) are suffered to enter the surface of contact which is formed between the elastic acoustic medium and the surface of the ultrasonic probe for transmitting and receiving an ultrasonic wave during the attachment of the ultrasonic coupler to the ultrasonic probe. The entrapped bubbles pose a problem that the transmission of an ultrasonic wave to the subject is not carried out favorably.

Again with respect to the shape of the ultrasonic coupler, since the cross section taken parallelly to the direction of ultrasonic scanning and also to the direction of transmission of an ultrasonic wave assumes a fixed rectangular shape or increases in width in the direction of transmission of an ultrasonic wave, the size of the ultrasonic coupler is limited to the visible dimensions of the ultrasonic probe and, as a result, the shape of the ultrasonic coupler is larger than the area in which the ultrasonic beam is transmitted and received. This fact constitutes itself a factor for degrading the contacting property of the ultrasonic coupler with the subject or the scanning property of the ultrasonic coupler on the subject.

An object of this invention, therefore, is to provide a novel ultrasonic coupler.

Another object of this invention is to provide an ultrasonic coupler which precludes the impairment of a produced image due to the retaining property of the elastic accoustic medium and the flexure of the elastic acoustic medium acoustic medium and the entrapment of bubbles during the attachment of the ultrasonic coupler to the ultrasonic probe and, which is more, improves the contacting property with the subject and the operability.

A further object of this invention is to provide an ultrasonic coupler which allows simple manufacture and easy handling and has been sterilized and a method for the production thereof.

SUMMARY OF THE INVENTION

The objects described above are accomplished, in an ultrasonic coupler provided with an ultrasonic wave propagating member formed of a water-containing polymeric gel and a holder for accommodating the propagating member and fixing it to a probe, by an ultrasonic coupler intended to be interposed between a subject under test and an ultrasonic probe for transmitting and receiving an ultrasonic wave to and from the subject under test and characterized by the fact that the ultrasonic wave propagating member is a water-containing polymeric gel produced by integrally cross-linking an aqueous solution of a water-soluble polymeric compound with the holder inside the holder.

These objects are further accomplished by a method for the production of an ultrasonic coupler to be interposed between a subject under test and an ultrasonic probe for transmitting and receiving an ultrasonic wave to and from the subject under test, which method is characterized by supplying an aqueous solution of a water-soluble polymeric compound into a holder of an ultrasonic coupler provided with an ultrasonic wave propagating member formed of a water-containing polymeric gel and the holder for accommodating the propagating member and fixing it to a probe and subsequently cross-linking the polymeric compound thereby forming a water-containing polymeric .gel in consequence of integrally cross-linking the polymeric compound with the holder inside the holder.

This invention further discloses an ultrasonic coupler and a method for the production thereof, wherein the cross-linking of the water-soluble polymeric compound is accomplished by exposure of the compound to a radiation, preferably to the $\gamma$ ray. This invention further discloses an ultrasonic coupler and a method for the production thereof, wherein the water-soluble polymeric compound is at least one member selected from the group consisting of polyvinyl alcohol, polyvinyl pyrrolidone, polyethylene oxide, polyacrylamide, polyacrylic acid, alkali metal salts of polyacrylic acid, and products of partial neutralization of polyacrylic acid with alkali metals.

The objects described above are further accomplished, in an ultrasonic coupler provided with an elastic acoustic medium intended to be interposed between an ultrasonic probe and a subject under test and possessed of surfaces for contact with both an ultrasonic wave-transmitting and -receiving surface of the ultrasonic probe and the subject under test and an immobilizing member adapted to accommodate the elastic acoustic medium, possessed of openings one each on the ultrasonic probe side and the subject side, and enabled to be attached to or detached from the ultrasonic probe, by an ultrasonic coupler characterized by the fact that the cross section of the elastic acoustic medium taken perpendicularly to the direction of transmission of an ultrasonic wave exceeds the area of the subject side opening of the immobilizing member and, at the same time, projects past the leading end of the immobilizing member.

This invention further discloses an ultrasonic coupler, wherein part or the whole of the surfaces of the elastic acoustic medium for contact with the ultrasonic wave-transmitting and -receiving surface of the ultrasonic probe possess a convexly curved contour. This invention further discloses an ultrasonic coupler, wherein attaching parts are disposed above the ultrasonic probe side opening part of the immobilizing member in such a manner as to contact at least a pair of opposed lateral surfaces of the ultrasonic probe and the interval between the opposed attaching parts is smaller than the width of the corresponding ultrasonic probe. This invention further discloses an ultrasonic coupler, wherein part or the whole of the lateral surfaces of the elastic acoustic medium are formed in a convex or concave contour and, at the same time, the corresponding inner walls of the immobilizing member are formed in a concave or convex contour. This invention further discloses an ultrasonic coupler, wherein the ultrasonic coupler is so shaped that the cross section of the ultrasonic coupler taken parallelly to the direction of ultrasonic scanning and also to the direction of ultrasonic wave transmission decreases in width in the direction of transmission of an ultrasonic wave.

The objects described above are further accomplished, in an ultrasonic coupler provided with an elastic acoustic medium intended to be interposed between an ultrasonic probe and a subject under test and possessed of surfaces for contact with both an ultrasonic wave-transmitting and -receiving surface of the ultrasonic probe and the subject under test and an immobilizing member adapted to accommodate the elastic acoustic medium, possessed of openings one each on the ultrasonic probe side and the subject side, and enabled to be attached to or detached from the ultrasonic probe, by an ultrasonic coupler characterized by the fact that part or the whole of the surfaces of the elastic acoustic medium for contact with the ultrasonic wave-transmitting and -receiving surface of the ultrasonic probe assumes a convexly curved contour, the elastic acoustic medium is so shaped as to be substantially flush with the leading end surface of the subject side opening part of the immobilizing member, and the elastic acoustic medium projects past the leading end surface of the opening part when the immobilizing member is attached to the ultrasonic probe.

This invention further discloses an ultrasonic coupler, wherein attching parts are disposed above the ultrasonic probe side opening part of the immobilizing member in such a manner as to contact at least a pair of opposed lateral surfaces of the ultrasonic probe and the interval between the opposed attaching parts is smaller than the width of the corresponding ultrasonic probe. As described above, this invention is directed to an ultrasonic coupler provided with an ultrasonic wave propagating member formed of a water-containing polymeric gel and a holder for accommodating the propagating member and fixing it to a probe, which ultrasonic coupler is intended to be interposed between a subject under test and an ultrasonic probe for transmitting and receiving an ultrasonic wave to and from the subject under test and characterized by the fact that the ultrasonic wave propagating member is a water-containing polymeric gel produced by integrally cross-linking an aqueous solution of a water-soluble polymeric compound with the holder inside the holder. This ultrasonic coupler is produced by supplying an aqueous solution of a water-soluble polymeric compound to the interior of the holder and then subjecting the polymeric compound to a cross-linking reaction thereby forming a water-containing polymeric gel integrally cross-linked with the holder inside the holder. The ultrasonic coupler, therefore, enjoys ease of handling because it obviates the necessity for attaching the ultrasonic wave propagating member fast to the holder each time the coupler is used on the probe. Even when the water-containing polymeric gel has low mechanical strength, it enjoys enhanced fastness of adhesion to the subject, imparts notably improved operability to the probe, and exhibits an improved efficiency in the transmission of an ultrasonic wave because this gel can be immobilized to the holder. Where the ultrasonic wave propagating member is cross-linked by being exposed to a radiation such as, for example, the ray, since the exposure to the radiation concurrently serves to sterilized the ultrasonic coupler, this ultrasonic coupler can be put directly to use in a surgical operation or in centesis which dictates sterilization.

This invention is further directed to an ultrasonic coupler provided with an elastic acoustic medium intended to be interposed between an ultrasonic probe and a subject under test and possessed of surfaces for contact with both an ultrasonic wave-transmitting and -receiving surface of the ultrasonic probe and the subject under test and an immobilizing member adapted to accommodate the elastic acoustic medium, possessed of openings one each on the ultrasonic probe side and the subject side, and enabled to be attached to or detached from the ultrasonic probe, which ultrasonic coupler is characterized by the fact that the cross section of the elastic acoustic medium taken perpendicularly to the direction of transmission of an ultrasonic wave exceeds the area of the subject side opening of the immobilizing member and, at the same time, projects past the leading end of the immobilizing member. The ultrasonic coupler provided by this invention, therefore, is enabled to establish contact very satisfactorily with the subject under test, retain the elastic acoustic medium with improved fastness therein, ensure highly satisfactory fulfilment of the transmission and reception of an ultrasonic wave, and facilitate the prevention of entrapment of bubbles during the attachment of the ultrasonic coupler to the ultrasonic probe and the location of the ultrasonic coupler relative to the ultrasonic wave-transmitting and -receiving surface of the ultrasonic probe.

Further, this invention is directed to an ultrasonic coupler provided with an elastic acoustic medium intended to be interposed between an ultrasonic probe and a subject under test and possessed of surfaces for contact with both an ultrasonic wave-transmitting and -receiving surface of the ultrasonic probe and the subject under test and an immobilizing member adapted to accommodate the elastic acoustic medium, possessed of openings one each on the ultrasonic probe side and the subject side, and enabled to be attached to or detached from the ultrasonic probe, which ultrasonic coupler is characterized by the fact that part or the whole of the surfaces of the elastic acoustic medium for contact with the ultrasonic wave-transmitting and -receiving surface of the ultrasonic probe assumes a convexly curved contour, the elastic acoustic medium is so shaped as to be substantially flush with the leading end surface of the subject side opening part of the immobilizing member, and the elastic acoustic medium projects past the leading end surface of the opening part when the immobilizing member is attached to the ultrasonic probe. The ultrasonic coupler, therefore, enjoys the advantage that, while the ultrasonic coupler is not in use, the elastic acoustic medium has a very remote possibility of contacting other objects and consequently keeps the leading end surface thereof from defilement and, after the ultrasonic coupler has been attached to the ultrasonic probe, the insertion of the ultrasonic probe under pressure results in projecting the elastic acoustic medium from the leading end surface of the subject side opening of the immobilizing member and consequently forming a desired projected part and enabling the elastic acoustic medium to contact the subject under test very satisfactorily.

BRIEF DESCRIPTION OF THE DRAWINGS

FIG. 1A is a cross section of a conventional ultrasonic coupler.

FIG. 1B is a side elevation of the ultrasonic coupler of FIG. 1A.

FIGS. 2A to 2C are cross sections each of a varying conventional ultrasonic coupler.

FIG. 3 is a cross section illustrating an ultrasonic coupler of the present invention in a state undergoing the process of production.

FIG. 4A is a cross section of the ultrasonic coupler of the present invention.

FIG. 4B is a side elevation of the ultrasonic coupler of FIG. 4A.

FIG. 5 is a cross section illustrating the ultrasonic coupler of the present invention in a state undergoing the process of use.

FIGS. 6A to 6C are cross sections each illustrating a varying ultrasonic coupler as other embodiment of the present invention.

FIG. 7 is a cross section illustrating the ultrasonic coupler of FIG. 6B in a state undergoing the process of use.

FIG. 8A is a cross section illustrating an ultrasonic coupler as yet another embodiment of this invention.

FIG. 8B is a cross section illustrting the ultrasonic coupler of FIG. 8A in a state undergoing the process of use.

FIG. 9 is an exploded perspective view illustrating an ultrasonic coupler as still another embodiment of this invention.

FIG. 10A is a cross section taken through FIG. 9 along the line Xa—Xa, illustrating the ultrasonic coupler in a state having an elastic acoustic medium attached to a immobilizing member.

FIG. 10B is a cross section taken through FIG. 10A along the line Xb—Xb.

EXPLANATION OF THE PREFERRED EMBODIMENT

Figure 11A:
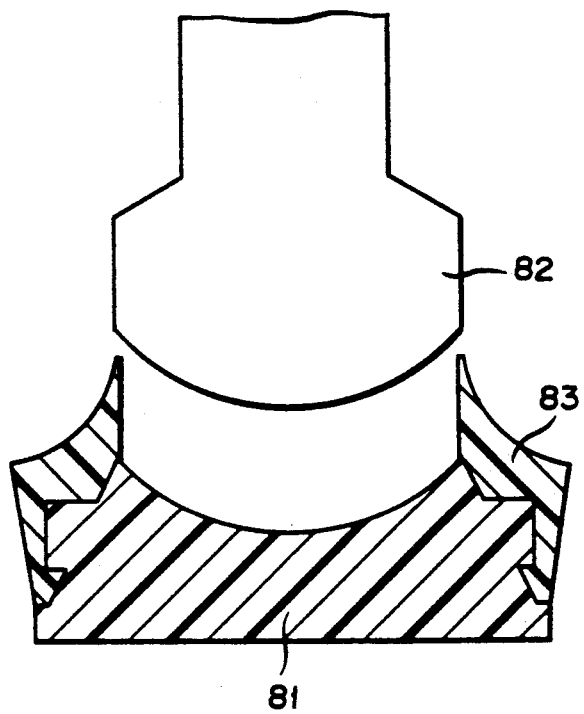
FIG. 11A and FIG. 11B are cross sections illustrating a further embodiment of this invention.

This invention concerns an ultrasonic coupler provided with an ultrasonic wave propagating member formed of a water-containing polymeric gel and a holder for accommodating the propagating member and fixing it to a probe, which ultrasonic coupler is intended to be interposed between a subject under test and an ultrasonic probe for transmitting and receiving an ultrasonic wave to and from the subject under test and characterized by the fact that the ultrasonic wave propagating member is a water-containing polymeric gel produced by integrally cross-linking an aqueous solution of a water-soluble polymeric compound with the holder inside the holder. This ultrasonic coupler is produced by supplying an aqueous solution of a water-soluble polymeric compound to the interior of the holder and then subjecting the polymeric compound to a cross-linking reaction thereby forming a water-containing polymeric gel integrally cross-linked with the holder within the holder.

The water-soluble polymeric compounds which are effectively usable in this invention include polyvinyl alcohol, polyvinyl pyrrolidone, polyethylene oxide, polyacrylamide, polyacrylic acid, alkali metal salts of polyacrylic acid, and products of partial neutralization of polyacrylic acid with alkali metals. In all of the water-soluble polymeric compounds cited above, polyethylene oxide proves to be most preferable. The molecular weight of this polyethylene oxide is required to exceed 100,000 and desired to be in the range of 200,000 to 8,000,000.

The cross-linking of the water-soluble polymeric compound can be carried out by various method. A method which effects this reaction with a polyfunctional isocyanate compound or a polyfunctional epoxy compound, a method which effects this reaction by irradiation with a radiation, and a method which effects the reaction by freezing and defrosting the compound may be cited, for example. Among other methods mentioned above, the method resorting to the exposure to a radiation proves to be particularly preferable in the sense that this exposure fulfils sterilization concurrently with the cross-linking.

The cross-linking by the exposure to a radiation is accomplished by placing an aqueous solution of the water-soluble polymeric compound in the aforementioned holder and exposing this aqueous solution to a radiation thereby three-dimensionally cross-linking the polymer and allowing 80 to 99% by weight, preferably 90 to 98% by weight, of water to be contained in the reticular texture of the resultant cross-linked polymer. The reason for this range of water content is that the ultrasonic wave is attenuated to an unduly large extent if the water content is less than 80% by weight and the mechanical strength of the ultrasonic wave propagating medium is inferior if the water content exceeds 99% by weight. The concentration of the water-soluble polymeric compound in the aforementioned aqueous solution is in the range of 1 to 20% by weight, preferably 2 to 10% by weight. Optionally, the aqueous solution may incorporate therein an antiseptic and a stabilizer.

The radiations which are effectively usable herein for the sake of the cross-linking include $\gamma$-ray and elecrtron beam, for example. The $\gamma$-ray proves to be more preferable than the electron beam. The dosage of the radiation is in the range of 0.25 to 2.5 Mrads, preferably 0.5 to 1.5 Mrads. The reason for this range of dosage is that the cross-linking does not proceed to a sufficient degree and the product of this cross-linking reaction holds the shape of its own only with difficulty if the dosage is less than 0.25 Mrad and the product of the cross-linking reaction gains excessively in rigidity, exhibits insufficient flexibility, and suffers from unduly low fastness of adhesion to the contour of a given site for contact.

The water contents mentioned in the present specification were determined in accordance with the following formula.

$$\text{Water content (\%)} = \frac{\text{Weight of water-containing gel} - \text{Weight of dry gel}}{\text{Weight of water-containg gel}} \times 100$$

The holder is generally made of a thermoplastic resin such as, for example, polycarbonate, polystyrene, or polypropylene.

Now, embodiments of the present invention will be described below with reference to the accompanying drawings.

FIGS. 3 to 5 represent one embodiment of this invention. First, as illustrated in FIG. 3, a lower opening part 11 of a holder 12 which has the opening part 11 provided in the bottom part thereof is closed by having a lower lid 13 tacked optionally by the use of an adhesive agent or helically attached thereto. Then, an aqueous solution of a water-soluble polymeric compound 14 is poured into the holder through an upper opening part 15. Subsequently, as illustrated in FIG. 4A and FIG. 4B, an upper lid 16 is inserted through the upper opening part 15 and fixed in such a manner as to establish tight contact throughout with the surface of the aforementioned aqueous solution 14. The aqueous solution 14 as retained in the holder 12 is either exposed to a radiation or frozen and defrosted to cross-link and solidify the water-soluble polymeric compound and give rise to an ultrasonic wave propagating member 17 formed of a water-containing polymeric gel. As a result, an ultrasonic coupler is obtained which has the water-containing polymeric compound 17 integrally cross-linked with the holder 12.

In FIG. 5, the use of the ultrasonic coupler which has been produced as described above is accomplished by removing the upper and lower lids 13 and 16, inserting a probe 18 through the upper opening part 15, fixing an acoustic radiation surface 19 of the probe 18 tightly in the ultrasonic wave propagating member 17, and then manipulating the probe 17 while keeping a contact surface 21 between the ultrasonic wave propagating member 17 and a subject 20 under test in tight adhesion to the subject 20 under test. The use of the ultrasonic coupler constructed as described above can be readily attained simply by fixing the holder 12 to the probe 18 because the holder 12 and the ultrasonic wave propagating member 17 are integrally joined.

FIGS. 6A to 6C represent another embodiment of this invention. First, an ultrasonic coupler illustrated in FIG. 6A is similar to the ultrasonic coupler shown in FIG. 4A, except that a stopper part 43 is formed in an ultrasonic wave propagating member 37 by digging at least one depressed part 42 wholly or partly in circumference in the inner wall of a holder 32. Then, an ultrasonic coupler illustrated in FIG. 6B is similar to the ultrasonic coupler shown in FIG. 6B, except that the leading end part (a lower opening part 31) of the ultrasonic wave propagating member 37 is formed in an area larger than the area of the opening part just mentioned. Thus, the fasstness of adhesion is further enhanced because the leading end part of the holder 32 is not suffered to contact a subject 40 under test as illustrated in FIG. 7. Further, an ultrasonic coupler illustrated in FIG. 6C is similar to the ultrasonic coupler shown in FIG. 6A, except that the effectiveness of contact of the surface of the ultrasonic wave propagating member 37 with the leading end part of a probe 38 is enhanced by using an upwardly curved upper lid 36 thereby allowing the resultantly formed ultrasonic wave propagating member 37 to acquire an upwardly curved surface. FIG. 8A and FIG. 8B represent still other embodiments of this invention. Since the lower part of a holder 52 has a downwardly increased diameter, for the purpose of preventing an ultrasonic wave propagating member 57 from falling down, a stopper part 63 is formed in the ultrasonic wave propagating member 57 by digging at least one depressed part 62 wholly or partly in circumference in the inner wall of the holder 52. Further, since the width of a surface 61 of the ultrasonic wave propagating member 57 for contact with a subject 60 under test is larger than a lower opening part 51 of the holder 52, the holder 52 has no possibility of contacting the subject 60 under test and, as the result, the fastness of contact with the subject 60 is further enhanced. Since, in this case, the subject side opening part (lower opening part) 51 is larger than the probe side opening part (upper opening part) 55, the multiple reflection of an ultrasonic wave on the inner wall of the holder 52 is inconspicuous.

In FIGS. 6A to 7 and FIGS. 8A dn 8B, the reference numerals which are the sums of the reference numerals of FIGS. 3 to 5 plus 20 and 40 denote the identical component parts to those shown in the latter diagrams.

An ultrasonic coupler illustrated in FIG. 9, FIG. 10A, and FIG. 10B as representing another embodiment of this invention comprises an elastic acoustic medium 71 solidified in the form of gel and an immobilizing member 73 capable of causing this elastic acoustic medium 71 to be attached fast to and detatched from an ultrasonic wave-transmitting and -receiving surface 72a of an ultrasonic probe 72. The elastic acoustic member 71 has the widths Wa and Wb of a surface 71b thereof for contact with a subject under test enlarged beyond the widths Wa' and Wb' of the subject side opening of the part of the immobilizing member 73 medium 71 accommodating the elastic acoustic and the elastic acoustic member 71 protrudes from the leading end of the immobilizing member 73. More specifically, the cross section of the elastic acoustic medium 71 taken along a direction perpendicular to the direction of transmission of an ultrasonic wave from the elastic acoustic medium 71 exceeds the area of the subject side opening of the immobilizing member 73 and protrudes past the leading end of the immobilizing member 73.

As a result of forming the elastic acoustic medium 71 as described above, the subject side surface 73a of the immobilizing member 73 is destined to press down a peripheral part 71c of the elastic acoustic medium 71 when the ultrasonic coupler is moved on the subject. Consequently, the flexure (deformation) of the elastic acoustic medium 71 is lessened and the otherwise possible impairment of propagation of an ultrasonic wave can be precluded by the retaining property and flexure of the elastic acoustic medium 71. Further, the part 71a of the elastic acoustic medifum 71 for contact with the ultrasonic wave-transmitting and -receiving surface 72a of the ultrasonic probe 72 is convexly curved. On the lateral surfaces of the elastic acoustic medium 71, convex parts 71d or concave parts (not shown) corresponding to the concave parts 73d or convex parts (not shown) of the immobilizing member 73 are formed one each.

The immobilizing member 73 is formed of a hard plastic substance such as, for example, polycarbonate, polystyrene, or polypropylene. In the part 73b for accommodation of the ultrasonic probe 72, the immobilizing member 73 parallel to the visible dimensions of the ultrasonic probe 73 possesses widths Da and Db. An attaching part 73b for the ultrasonic probe 72 is formed on at least one pair of opposed lateral surfaces in the lateral surfaces of the opening. This attaching part 73b is so formed that the interval L between the opposed lateral surfaces is smaller than the width L' of the corresponding ultrasonic probe 72. The immobilizing member 73, owing to the elasticity thereof, nips the ultrasonic probe 72. Further, as illustrated in FIG. 10A and FIG. 10B, concave parts 73d conforming to the convex parts 71d of the lateral surfaces of the elastic acoustic medium 71 are formed on the inner walls. The elastic acoustic medium 71 is immobilized by fitting into the concave parts 73d the convex parts 71d formed on the lateral surfaces of the elastic acoustic medium 71. Otherwise, the immobilization of the elastic acoustic medium 71 is attained by supplying the aqueous solution mentioned above and cross-linking the polymeric compound in the aqueous solution integrally with the elastic acoustic medium 71. The cross section of the immobilizing member 73 taken in a direction perpendicular to the direction of ultrasonic scanning and also to the direction of transmission of an ultrasonic wave is decreased in width in the direction of transmission of an ultrasonic wave as illustrated in FIG. 10A.

This invention has been described with reference to one embodiment thereof. This invention need not be limited to this embodiment but may be suitably modified without departing from the spirit of the invention. For example, while this embodiment of the invention has been depicted as one having the convexly curved parts of the elastic acoustic medium 71 formed only in the cross section perpendicular to the direction of ultrasonic scanning, these curved parts may be formed in the cross section parallel to the direction of ultrasonic scanning or on the entire surface for contact with the ultrasonic wave-transmitting and -receiving surface. Further, the concave and convex parts formed on the lateral surfaces of the elastic acoustic medium 71 and the inner wall of the immobilizing member 73 may be otherwise formed on part or the whole of the lateral surfaces or the concave and convex parts may be formed inversely. While the attaching parts 73b for the ultrasonic probe 72 which are provided for the immobilizing member 73 are formed in the present embodiment only on one pair of opposed lateral surfaces, they may be formed on the four lateral surfaces perpendicularly intersecting the opening surface.

Figure 11B:
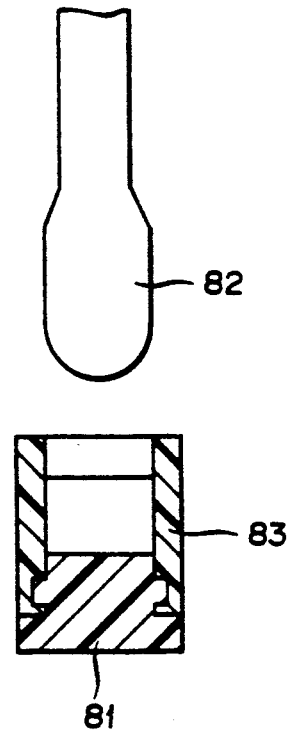

This invention may be adapted not merely for a linear array probe but also for a simple probe, a mechanical scan probe, and a convex probe, for example (Refer FIG. 11A and FIG. 11B. In these diagrams, the reference numerals which are the sums of the reference numerals of FIG. 9, FIG. 10A, and FIG. 10B plus 10 denote identical component parts.).

In the ultrasonic couplers illustrated in FIG. 9 to FIG. 11B as embodiments of this invention, the cross section of the elastic acoustic medium taken in a direction perpendicular to the direction of ultrasonic transmission is required to exceed the area of the subject side opening of the immobilizing member and protrude past the leading end of the immobilizing member. When this requirement is fulfilled, the surface of the edge defining the subject side opening part of the immobilizing member manifests the effect of pressing the part of the elastic acoustic medium protruding along the immobilizing member and enhancing the retaining property of the elastic acoustic medium. Further, since the flexure suffered to occur in the elastic acoustic medium during a movement of the ultrasonic coupler on the subject is depressed, the otherwise inevitable impairment of the transmission of an ultrasonic wave can be precluded.

Part or the whole of the surfaces of the elastic acoustic medium for contact with the ultrasonic wave-transmitting and -receiving surface of the ultrasonic probe are preferable to be formed in a convexly curved shape. Such convex surfaces serve the purpose of expelling bubbles (air) when the ultrasonic coupler is attached to the ultrasonic probe and consequently preventing bubbles from intervening between the ultrasonic wave-transmitting and -receiving surface of the ultrasonic probe and the elastic acoustic medium brought into contact therewith.

The width of the part of the immobilizing member for attachment of the ultrasonic probe is desired to be smaller than the width of the corresponding ultrasonic probe. When this desire is satisfied, the attaching part is allowed to nip the ultrasonic probe and prevent the otherwise possible deviation in the relative positions of the ultrasonic probe and the ultrasonic coupler. The retaining property of the elastic acoustic medium can be improved by forming part or the whole of the lateral surfaces of the elastic acoustic medium in a convex or concave shape and, at the same time, forming the corresponding inner walls of the immobilizing member in a concave or convex shape.

Figure 12A:
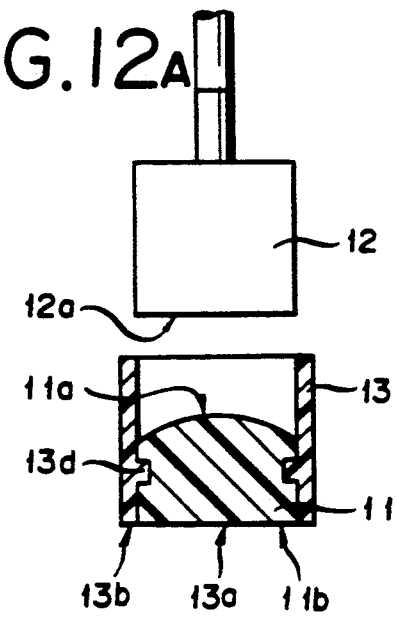
FIG. 12A is a cross section illustrating an ultrasonic coupler as still another embodiment of this invention.
Figure 12B:
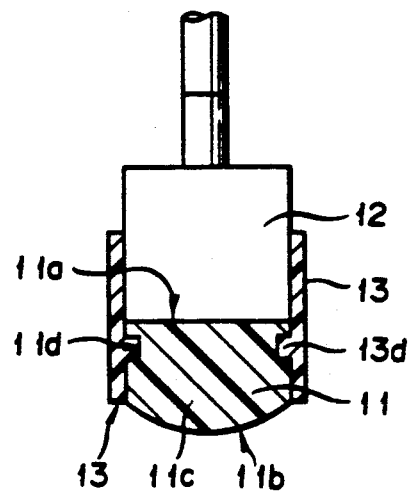
FIG. 12B is a cross section illustrating the ultrasonic coupler in a state of attachment to an ultrasonic probe.

An ultrasonic coupler illustrated in FIG. 12A and FIG. 12B as another embodiment of this invention comprises an elastic acoustic medium 91 solidified in the form of gel and an immobilizing member 93 capable of attaching fast and detaching the elastic acoustic medium 91 to and from an ultrasonic wave-transmitting and -receiving surface 92a of an ultrasonic probe 92. Part or the whole of the surfaces 91a of the elastic acoustic member 91 for contact with the ultrasonic wave-transmitting and -receiving surface assume a convexly curved shape. The subject side leading end surface 91b of the elastic acoustic medium 91 is so formed as to fall substantially flush with the leading end surface 93b of the subject side opening part 93a of the immobilizing member 93.

When the immobilizing member 93 is attached to the ultrasonic probe 92, the ensuant insertion (under pressure) of the ultrasonic probe causes the elastic acoustic medium 91 to protrude past the leading end surface 93b of the subject side opening of the immobilizing member 93 and give rise to the projected part 91c as desired. On the lateral surfaces of the elastic acoustic medium 91, concave parts 93d or convex parts (not shown) corresponding to the convex parts 93d or concave parts (not shown) of the immobilizing member 93 are formed.

The immobilizing member 93 is formed of a head plastic substance such as, for example, polycarbonate, polystyrene, or polypropylene.

This invention has been described with reference to an embodiment thereof. This invention, however, need not be limited to this embodiment but may be suitably modified without departing from the spirit of this invention.

For example, this invention may be adapted not only for a linear array probe but also for a single probe, a mechanical scan probe, and a convex probe.

The ultrasonic coupler illustrated in FIG. 12A and FIG. 12B as an embodiment of this invention is so constructed that part or the whole of the surfaces of the elastic acoustic medium for contact with the ultrasonic wave-transmitting and -receiving surface of the ultrasonic probe assume a convexly curved shape, the elastic acoustic medium is substantially flush with the leading end surface of the subject side opening part of the immobilizing member, and the elastic acoustic medium protrudes past the leading end surface of the opening part. When the ultrasonic coupler is not in use (namely when the ultrasonic coupler is not attached to the ultrasonic probe), therefore, the elastic acoustic medium has a very remote possibility of contacting other objects and is prevented from defilement. When the ultrasonic coupler is attached to the ultrasonic probe, the ensuant insertion (under pressure) of the ultrasonic probe causes the elastic acoustic medium to protrude past the leading end surface of the subject side opening of the immobilizing member and give rise to a desired projecting part and consequently permit creation of highly satisfactory contact between the elastic acoustic medium and the subject under test.

Further, when part or the whole of the surfaces of the elastic acoustic medium for contact with the ultrasonic wave-transmitting and -receiving surface of the ultrasonic probe are formed in a convexly curved shape, the curved surfaces have the effect of expelling bubbles (air) during the attachment of the ultrasonic coupler to the ultrasonic probe and consequently preventing otherwise inevitable intervention of bubbles between the ultrasonic wave-transmitting and -receiving surface of the ultrasonic probe and the elastic acoustic medium brought into contact therewith.

Now, the present invention will be described more specifically below with reference to working examples.

Wherever "%" is mentioned in the examples, it is meant as "% by weight" unless otherwise specified.

EXAMPLE 1

In 200 ml of deionized water, 6.0 g of polyethylene oxide (molecular weight 4,000,000) was dissolved by stirring at room temperature. A holder 2 made of polystyrene and constructed as illustrated in FIG. 3 was filled with the solution carefully to avoid entrance of bubbles. The solution in the holder was irradiated with 1.0 Mrad of γ ray to be cross-linked integrally with the holder 2. As the result, an ultrasonic coupler was produced and simultaneously sterilized. The ultrasonic wave propagating medium of the produced ultrasonic coupler was in the form of gel having no stickiness, containing no bubble, and exhibiting colorlessness and transparency. The water content was 97.1% and the density at 20° C. was 1.006 g/cm$^3$.

EXAMPLE 2

In 200 ml of deionized water, 10.0 g of polyethylene oxide (molecular weight 300,000), 0.1 g of sodium edetate, and 0.008 g of benzalkonium chloride as an antiseptic were dissolved. The resultant solution was supplied to a holder made of polycarbonate and constructed as illustrated in FIG. 6B and irradiated with the γ ray in the same manner as in Example 1. Consequently, there was obtained an ultrasonic coupler integrally provided with an ultrasonic wave propagating medium in the form of gel having no stickiness and exhibiting colorlessness and transparency. The water content was 95.2% and the density was 1.010 g/cm$^3$.

EXAMPLE 3

In 200 ml of deionized water, 10.0 g of polyethylene oxide (molecular weight 600,000), 0.05 g of sodium edetate, and 0.008 g of benzalkonium chloride as an antiseptic were dissolved. The resultant solution was supplied to a holder 2 made of polystyrene and constructed as illustrated in FIG. 8A and irradiated with 0.75 Mrad of the γ ray to be cross-linked integrally with the holder 2. As the ressult, an ultrasonic coupler was produced and simultaneously sterilized. The ultrasonic wave propagating medium of the produced ultrasonic coupler was in the form of gel having no stickiness, containing no bubble, and exhibiting colorlessness and transparency. The water content was 95.2% and the density at 20° C. was 1.010 g/cm$^3$.

What is claimed is:

1. An ultrasonic coupler for interposition between a test subject and an ultrasonic probe which transmits and receives ultrasonic waves to and from the test subject, said ultrasonic coupler comprising;
    an ultrasonic wave propagating member formed of a water-containing polymeric gel; and
    a holder for accommodating said propagating member and fixing it to an ultrasonic probe, said water-containing polymeric gel being an aqueous solution of a water-soluble polymeric compound integrally cross-linked with said holder inside said holder.

2. An ultrasonic coupler according to claim 1, wherein said water-soluble polymeric compound is cross-linked in three-dimensions by exposure of said water-soluble polymeric compound to radiation.

3. An ultrasonic coupler according to claim 1 or claim 2, wherein said water-soluble polymeric compound is selected from a group consisting of polyvinyl alcohol, polyvinyl pyrrolidone, polyethylene oxide, polyacrylamide, polyacrylic acid, alkali metal salts of polyacrylic acid, and products of partial neutralization of polyacrylic acid with alkali metals.

4. A method for the production of an ultrasonic coupler to be interposed between a subject under test and an ultrasonic probe for transmitting and receiving an ultrasonic wave to and from said subject under test, which method includes the steps of:
    supplying an aqueous solution of a water-soluble polymeric compound into a holder of an ultrasonic coupler; and
    forming an ultrasonic wave propagating member as a water-containing polymeric gel, said holder accommodating said propagating member and fixing said propagating member to said ultrasonic probe, said step of forming an ultrasonic wave propagating member further including a step of forming said water-containing polymeric gel by integrally cross-linking said water-soluble polymeric compound with said holder inside said holder.

5. A method according to claim 4, wherein said cross-linking of the water-soluble polymeric compound further includes a step of exposing said water-soluble polymeric compound to radiation.

6. A method according to claim 4 or claim 5, wherein said water-soluble polymeric compound is selected from a group consisting of polyvinyl alcohol, polyvinyl pyrrolidone, polyethylene oxide, polyacrylamide, polyacrylic acid, alkali metal salts of polyacrylic acid, and products of partial neutralization of polyacrylic acid with alkali metals.

7. An ultrasonic coupler for interposition between an ultrasonic probe and a subject under test comprising:
    an elastic acoustic medium having surfaces for contact with both an ultrasonic wave-transmitting and -receiving surface of an ultrasonic probe and with a subject under test; and
    an immobilizing member for accomodating said elastic acoustic medium and adapted for attachment with said ultrasonic probe, said immobilizing member further including an opening for facing said ultrasonic probe and an opening for facing said test subject, a cross section of said elastic acoustic medium taken perpendicularly to a direction of transmission of an ultrasonic wave exceeding an area of the opening of said immobilizing member facing said test subject and projecting beyond an end of said immobilizing member.

8. An ultrasonic coupler according to claim 7, wherein at least a portion of a surface of said elastic acoustic medium for contacting the ultrasonic wave-transmitting and -receiving surface of said ultrasonic probe possesses a convexly curved contour.

9. An ultrasonic coupler according to claim 7 or claim 8, wherein said immobilizing member further includes opposed attaching parts disposed above the opening for facing the ultrasonic probe in such a manner as to contact at least a pair of opposed lateral surface of said ultrasonic probe, an interval between the opposed attaching parts being smaller than a width of the ultrasonic probe.

10. An ultrasonic coupler according to claim 7, wherein at least a portion of lateral surfaces of said elastic acoustic medium are formed in a convex or concave contour and, corresponding inner walls of said immobilizing member are formed in a concave or convex contour.

11. An ultrasonic coupler according to claim 7 or claim 8, wherein said ultrasonic coupler is shaped such that a cross-section of the ultrasonic coupler taken parallel to a direction of ultrasonic scanning and to a direction of ultrasonic wave transmission decreases in width in the direction of transmission of an ultrasonic wave.

12. An ultrasonic coupler for interposition between an ultrasonic probe and a subject under test comprising:
an elastic acoustic medium having surfaces for contact with both an ultrasonic wave-transmitting and -receiving surface of an ultrasonic probe and with a subject under test; and
an immobilizing member for attachment with said ultrasonic probe and adapted to accommodate said elastic acoustic medium, said immobilizing member including an opening for facing said ultrasonic probe and an opening for facing the subject, at least a portion of the surfaces of said elastic acoustic medium for contacting the ultrasonic wave-transmitting and -receiving surface of said ultrasonic probe having a convexly curved contour, said elastic acoustic medium being shaped substantially flush with an end surface of the opening of said immobilizing member facing the test subject, and said elastic acoustic medium projecting beyond the end surface of the opening when said immobilizing member is attached to said ultrasonic probe.

13. An ultrasonic coupler according to claim 12, wherein at least a portion of lateral surfaces of said elastic acoustic medium are formed in a convex or concave contour, with corresponding inner walls of said immobilizing member being formed in a concave or convex contour, respectively.

* * * * *